United States Patent
Liu et al.

(10) Patent No.: US 9,115,987 B2
(45) Date of Patent: Aug. 25, 2015

(54) OPTICAL METROLOGY WITH MULTIPLE ANGLES OF INCIDENCE AND/OR AZIMUTH ANGLES

(71) Applicant: Nanometrics Incorporated, Milpitas, CA (US)

(72) Inventors: Zhuan Liu, Fremont, CA (US); Shifang Li, Pleasanton, CA (US)

(73) Assignee: Nanometrics Incorporated, Milpitas, CA (US)

( * ) Notice: Subject to any disclaimer, the term of this patent is extended or adjusted under 35 U.S.C. 154(b) by 38 days.

(21) Appl. No.: 14/097,005

(22) Filed: Dec. 4, 2013

(65) Prior Publication Data

US 2015/0153165 A1    Jun. 4, 2015

(51) Int. Cl.
  *G01J 4/00* (2006.01)
  *G01B 11/26* (2006.01)
  *G01N 21/21* (2006.01)

(52) U.S. Cl.
  CPC ............. *G01B 11/26* (2013.01); *G01N 21/21* (2013.01)

(58) Field of Classification Search
  CPC ........................................................ G01J 4/00
  USPC ........................................................ 356/369
  See application file for complete search history.

(56) References Cited

U.S. PATENT DOCUMENTS

| | | | |
|---|---|---|---|
| 5,596,411 A | 1/1997 | Fanton et al. | |
| 5,889,593 A | 3/1999 | Bareket | |
| 6,600,560 B2 * | 7/2003 | Mikkelsen et al. | 356/369 |
| 6,798,512 B2 | 9/2004 | Ebert et al. | |
| 6,859,278 B1 | 2/2005 | Johs et al. | |
| 7,046,376 B2 | 5/2006 | Sezginer | |
| 7,068,363 B2 | 6/2006 | Bevis et al. | |
| 7,463,369 B2 * | 12/2008 | Wack et al. | 356/625 |
| 7,477,372 B2 | 1/2009 | Leslie et al. | |
| 7,483,133 B2 | 1/2009 | Bareket et al. | |
| 7,561,282 B1 | 7/2009 | Widmann | |
| 8,040,511 B1 | 10/2011 | Krishnan et al. | |

(Continued)

FOREIGN PATENT DOCUMENTS

JP    2001-004534 A    1/2001

OTHER PUBLICATIONS

Patent Abstracts of Japan for JP 2001-004534 published on Jan. 12, 2001 by NEC Corporation visited at <www.epo.org> on Jul. 19, 2013, 22 pages.

(Continued)

*Primary Examiner* — Roy M Punnoose
(74) *Attorney, Agent, or Firm* — Silicon Valley Patent Group LLP (57) ABSTRACT

An optical metrology device simultaneously detects light with multiple angles of incidence (AOI) and/or multiple azimuth angles to determine at least one parameter of a sample. The metrology device focuses light on the sample using an optical system with a large numerical aperture, e.g., 0.2 to 0.9. Multiple channels having multiple AOIs and/or multiple azimuth angles are selected simultaneously by passing light reflected from the sample through a plurality of pupils in a pupil plate. Beamlets produced by the plurality of pupils are detected, e.g., with one or more spectrophotometers, to produce data for the multiple AOIs and/or multiple azimuth angles. The data for multiple AOI and/or multiple azimuth angles may then be processed to determine at least one parameter of the sample, such as profile parameters or overlay error.

25 Claims, 6 Drawing Sheets

(56) References Cited

U.S. PATENT DOCUMENTS

| | | | |
|---|---|---|---|
| 2002/0027657 A1* | 3/2002 | Mikkelsen et al. | 356/369 |
| 2007/0002465 A1* | 1/2007 | Chuang et al. | 359/726 |
| 2007/0263219 A1 | 11/2007 | De Martino et al. | |
| 2009/0279090 A1* | 11/2009 | Wolf et al. | 356/369 |
| 2013/0003068 A1* | 1/2013 | Krishnan et al. | 356/445 |
| 2013/0321810 A1* | 12/2013 | Wang et al. | 356/369 |

OTHER PUBLICATIONS

International Search Report and Written Opinion mailed on Feb. 26, 2015 for International Application No. PCT/US2014/064687 filed on Nov. 7, 2014 by Nanometrics Incorporated, 12 pages.

* cited by examiner

OPTICAL METROLOGY WITH MULTIPLE ANGLES OF INCIDENCE AND/OR AZIMUTH ANGLES

FIELD OF THE INVENTION

The invention relates to an optical metrology, and more particularly to an optical metrology tool with multiple angles of incidence and/or azimuth angles.

BACKGROUND

The semiconductor industry, as well as other complex nanotechnology process industries, requires very tight tolerances in process control. As dimensions of chips continue to shrink, the tolerance requirements continue to become tighter. Accordingly, new more precise ways of measuring very small dimensions, e.g., on the order of a few nanometers, are desired. At this scale, typical microscopies, such as optical microscopy, or Scanning Electron Microscopy, are not suitable to obtain the desired precision, or to make quick, non-invasive measurements, which are also desirable.

Optical metrology techniques have been presented as a solution. The basic principle of optical metrology techniques is to reflect and/or scatter light from a target, and measure the resulting light. The received signal can be based simply on the reflectance of the light from the sample, or the change in polarization state (Psi, Delta) of the light caused by the sample. The light may be modeled to retrieve the geometries or other desired parameters of the illuminated sample.

With the continuously shrinking of critical dimensions in semiconductor devices and the industry moving to 3D device structures, optical metrology that is used to measure device structure parameters is facing more and more challenges due to lack of parameter sensitivity or strong parameter correlations. Continued improvements in optical metrology are therefore desirable.

SUMMARY

An optical metrology device simultaneously detects light with multiple angles of incidence (AOI) and/or multiple azimuth angles to determine at least one parameter of a sample. The metrology device focuses light on the sample using an optical system with a large numerical aperture, e.g., 0.2 to 0.9. Multiple channels having multiple AOIs and/or multiple azimuth angles are selected simultaneously by passing light reflected from the sample through a plurality of pupils in a pupil plate. Beamlets produced by the plurality of pupils are detected, e.g., with one or more spectrophotometers, to produce data for the multiple AOIs and/or multiple azimuth angles. The data for multiple AOI and/or multiple azimuth angles may then be processed to determine at least one parameter of the sample, such as profile parameters or overlay error.

In one implementation, an optical metrology device includes a light source that produces a beam of light; an optical system that focuses the beam of light into a spot on a sample, the optical system having a numerical aperture ranging from 0.2 to 0.9; a pupil plate having a plurality of pupils that simultaneously receives the beam of light after interacting with the sample, wherein a portion of the beam of light passes through each of the plurality of pupils as a beamlet, the plurality of pupils being arranged to produce beamlets at a plurality of at least one of angles of incidence and azimuth angles; at least one detector positioned to receive the beamlets; and a processor coupled to receive data from the at least one detector for the plurality of at least one of angles of incidence and azimuth angles, the processor configured to determine at least one parameter of the sample based on the data for the plurality of at least one of angles of incidence and azimuth angles.

In one implementation, a method includes producing a beam of light; focusing the beam of light to be incident on a spot on a sample using an optical system with a numerical aperture ranging from 0.2 to 0.9; simultaneously selecting multiple channels having at least one of different angles of incidence and different azimuth angles by passing the beam of light through a plurality of pupils in a pupil plate after the beam of light interacts with the sample to produce a plurality of beamlets having the at least one of different angles of incidence and different azimuth angles; detecting the plurality of beamlets to produce data for the at least one of different angles of incidence and different azimuth angles; and processing the data for the at least one of different angles of incidence and different azimuth angles to determine at least one parameter of the sample.

In one implementation, an optical metrology device includes a light source that produces a beam of light; an optical system that focuses the beam of light into a spot on a sample, the optical system having a numerical aperture ranging from 0.2 to 0.9; a channel selector configured to receive the beam of light after interacting with the sample and simultaneously selecting multiple channels having at least one of different angles of incidence and different azimuth angles; at least one detector positioned to detect the multiple channels to produce data for the at least one of different angles of incidence and different azimuth angles; and a processor coupled to receive the data from the at least one detector, the processor configured to determine at least one parameter of the sample based on the data for the at least one of different angles of incidence and different azimuth angles.

DETAILED DESCRIPTION

Figure 1A:
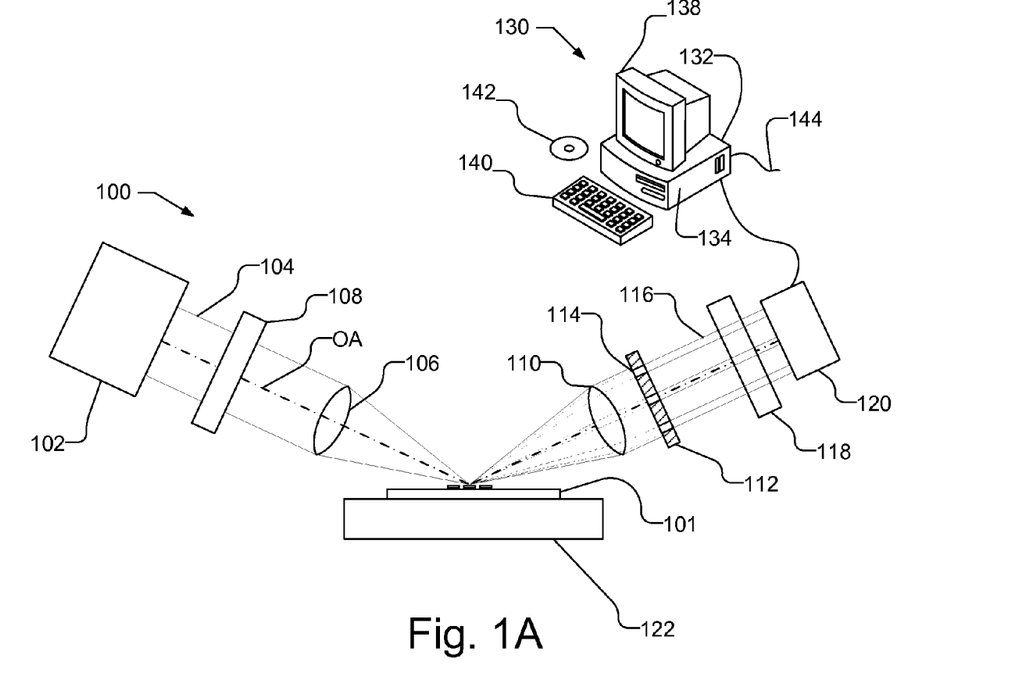
FIGS. 1A and 1B illustrate a side view and top view of an optical metrology device that measures one or more parameters of the sample by simultaneously selecting multiple channels having different angles of incidence and/or different azimuth angles.

FIG. 1A illustrates a side view of an optical metrology device 100 that measures one or more parameters of the sample 101 using a plurality of angles of incidence (AOI). The metrology device 100 includes a light source 102 that produces a collimated beam of light 104 along an optical axis, illustrated as line OA. The angle between the line OA and the wafer normal may be in the range from, e.g., 10 to 75 degrees. The light source 102 may be a broadband light source producing a plurality of wavelengths, e.g., a Xenon Arc lamp, a Deuterium lamp, a laser driven light source etc., may be used to produce light with a range of 190-3500 nm. If desired, however, the light source 102 may produce a single wavelength or multiple discrete wavelengths. The beam of light 104 is focused into a spot on the sample 101 with optical system 106, illustrated as a single lens 106, but multiple lenses may be used. Moreover, while FIG. 1A illustrates the use of a refractive optical system, a reflective optical system or a combination of refractive and reflective optical system may be used. The optical system 106 has a large numerical aperture (NA), e.g., that may range from 0.2 to 0.9, which corresponds to a full cone angle of the optical beam of 23 to 128°. The metrology device 100 may include a polarizer state controller 108 through which the beam of light 104 passes before being incident on the sample 101, e.g., positioned between the light source 102 and the optical system 106. The polarization state controller 108 may include a polarizer, and if desired, a compensator, either or both of which may be rotatable.

On the collection side, i.e., after the beam of light 104 is incident on and interacts with the sample 101, the beam of light 104 is collimated with collection optical system 110, again illustrated as a single refractive lens 110, but multiple lenses (reflective and/or refractive) may be used. A multiple channel selector is used to collect multiple AOIs and/or azimuth data. The multiple channel selector may be, e.g., a pupil plate 112 that includes a plurality of pupils 114 arranged to select the desired channels, e.g., multiple angles of incidence. Channels are selected by a portion of the collimated beam of light 104 passing through the pupils 114 to form a separate beamlet 116 for each channel. Each beamlet 116 (i.e., selected channel) corresponds to a different small cone angle of incident and reflected light. FIG. 1A illustrates the cone angle that corresponds to each beamlet 116 with dotted lines between the sample 101 and the pupil plate 112. As illustrated in FIG. 1A, the beamlets 116 corresponding to different angles of incidence are detected by one or more detectors 120, which may be a spectrometer. If desired, multiple detectors may be used, e.g., with each beamlet 116 being detected by a different detector. If desired, a polarization state analyzer 118 may be provided on the collection side, e.g., between the sample 101 and the detector 120.

Figure 1B:
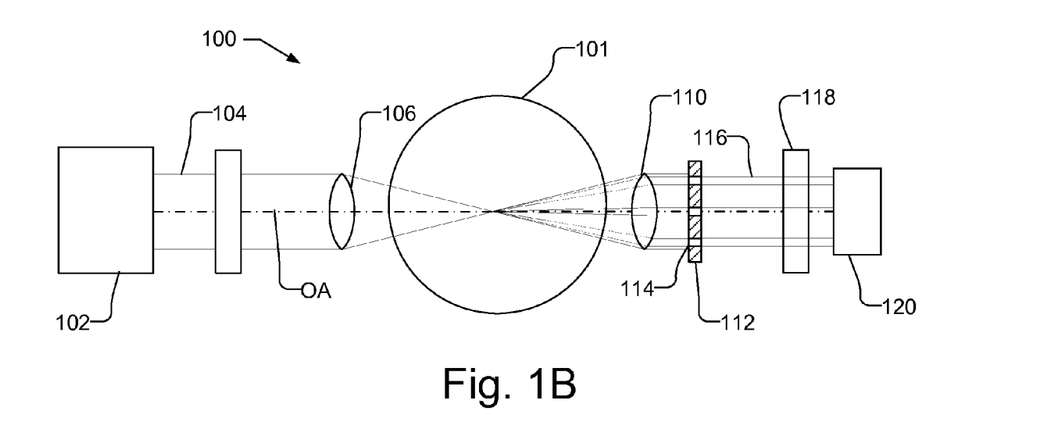

FIG. 1B illustrates a top view of the optical metrology device 100 and is similar to FIG. 1A, but illustrates optical metrology device 100 measuring the sample 101 using a plurality of azimuth angles. Thus, if desired, the pupil plate 112 of the metrology device 100 may be include a plurality of pupils arranged to simultaneously select channels that correspond to a plurality of AOIs (as illustrated in FIG. 1A) and a plurality of azimuth angles (as illustrated in FIG. 1B). If desired, the number of AOIs and the number of azimuth angles may be configured to be the same or different. If desired, however, the pupil plate 112 may be configured to limit the selected changes to only multiple AOIs or only azimuth angles.

The one or more detectors 120 simultaneously detect each beamlet corresponding to the selected channel. Thus, the one or more detectors 120 produces a plurality of data sets corresponding to each selected AOI and/or each selected azimuth angle. The one or more detectors 120 are coupled to provide the plurality of data sets to a computer 130, which includes a processor 132 with memory 134, as well as a user interface including e.g., a display 138 and input devices 140. A non-transitory computer-usable medium 142 having computer-readable program code embodied may be used by the computer 130 for causing the processor to control the metrology device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 142, which may be any device or medium that can store code and/or data for use by a computer system such as processor 132. The computer-usable medium 142 may be, but is not limited to, magnetic and optical storage devices such as disk drives, magnetic tape, compact discs, and DVDs (digital versatile discs or digital video discs). A communication port 144 may also be used to receive instructions that are used to program the computer 130 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Figure 2:
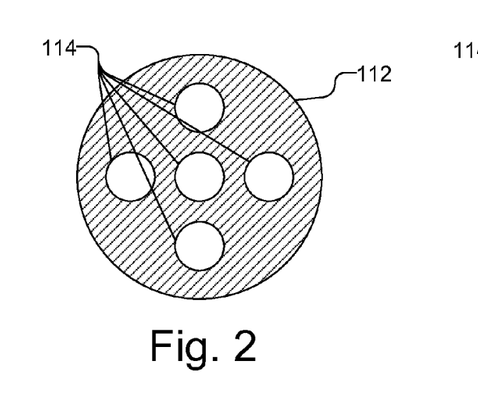
FIGS. 2, 3, 4, and 5 illustrate different embodiments of a channel selector in the form of a pupil plate having a plurality of pupils arranged to select different angles of incidence and/or different azimuth angles.
Figure 3:
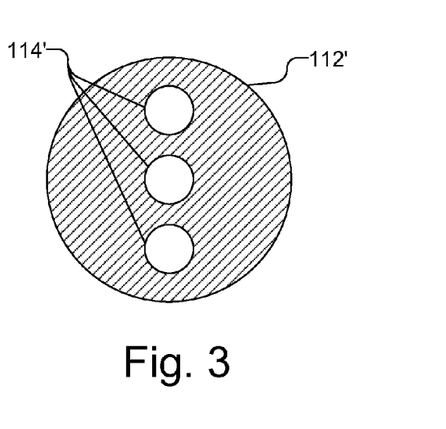
Figure 4:
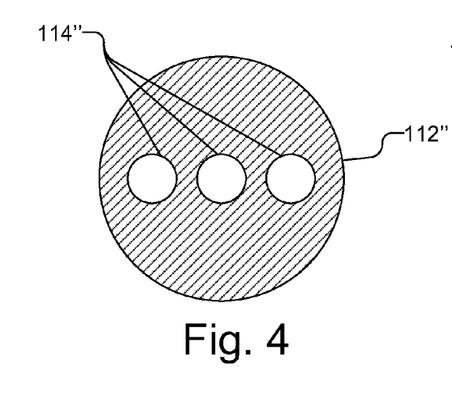
Figure 5:
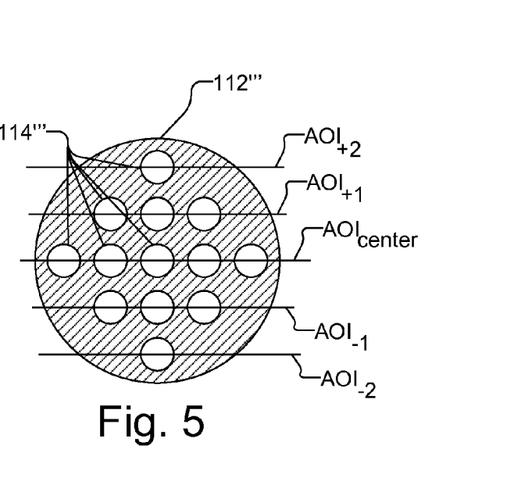

FIG. 2, by way of example, illustrates a plan view of the pupil plate 112, illustrated in FIGS. 1A and 1B, that includes a plurality of pupils 114 configured to simultaneously select a plurality of AOIs and a plurality of azimuth angles. FIG. 3, by way of example, illustrates a plan view of another example of a pupil plate 112' that includes a plurality of pupils 114' configured to simultaneously select a plurality of AOIs. FIG. 4 illustrates a plan view of another embodiment of the pupil plate 112" that includes a plurality of pupils 114" configured to simultaneously select a plurality of azimuth angles. As illustrated in FIGS. 2, 3, and 4, the pupil plate 112 is configured to simultaneously select three AOIs and/or three azimuth angles. If desired, however, additional AOIs and/or azimuth angles may be selected. FIG. 5, by way of example, illustrates a plan view of another embodiment of pupil plate 112''' that includes a number of pupils 114''' that is sufficient to simultaneously select five AOIs and a different number of azimuth angles at different AOIs, e.g., five azimuth angles at the center AOI position ($AOI_{center}$) and three azimuth angles at the +1 and −1 AOI positions ($AOI_{+1}$ and $AOI_{-1}$), and one azimuth angle at the +2 and −2 AOI positions ($AOI_{+2}$ and $AOI_{-2}$). If desired, a subset of these pupils may be used or additional pupils 114 may be include in the pupil plate, e.g., with multiple azimuth angles associated with each AOI.

Figure 6:
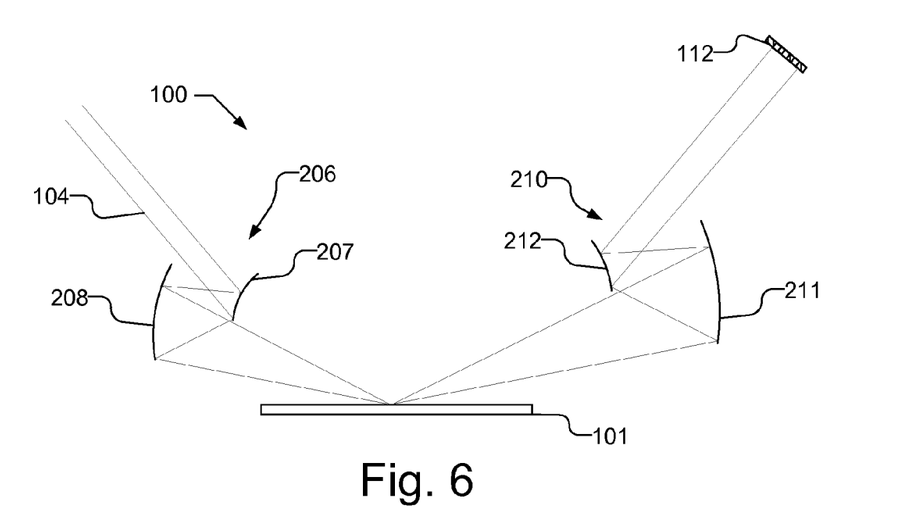
FIG. 6 is a side view of a portion of an optical metrology device using a reflective optical system with the channel selector.

As discussed above, the beam of light may be focused into a spot on the sample 101 using a reflective optical system. FIG. 6, by way of example, illustrates a portion of the beam path in the optical metrology device 100 in which a reflective optical system 206, including mirrors 207 and 208 are used to focus the beam of light 104 onto the sample 101. Reflective optical system 210, including mirrors 211 and 212, are used to collimate the beam of light 104 after interacting with the sample 101, and before the pupil plate 112. Similar to optical system 106 and 110 discussed with respect to FIG. 1A above, the focusing optical system 206 and collecting optical system 210 have a large NA, e.g., ranging from 0.2 to 0.9 or in another embodiment, with a full cone angle greater than 23°. Thus, it should be understood that any type of focusing and collecting optical system may be used.

Figure 7:
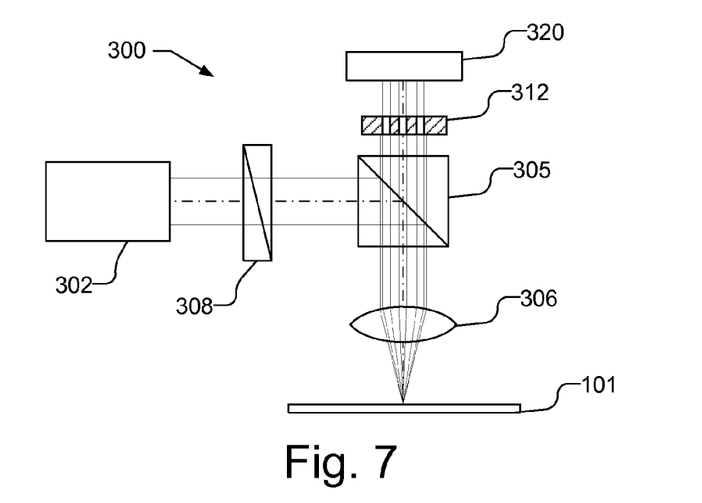
FIG. 7 is a side view illustrating a normal incidence optical metrology device capable of simultaneously selecting multiple channels.

Additionally, while FIGS. 1A and 1B illustrate the optical metrology device 100 measuring a plurality of AOIs and azimuth angles with obliquely incident light, normal incident light may be used as well. FIG. 7, by way of example, illustrates a normal incidence optical metrology device 300, which may be, e.g., a reflectometer, that includes a pupil plate 312 that acts as a multiple channel selector. Optical metrology device 300 includes a light source 302 that produces a collimated beam of light 304 along an optical axis, illustrated as line OA. As discussed above, the light source 302 may be a broadband light source. The beam of light 304 passes through a polarization state controller 308 which may be a polarizer. A beam splitter 305 directs at least a portion of the beam of light 304 towards the sample 101 and a lens 306, or series of lenses, with a large NA focuses the light on the sample 101. The light reflected from the sample is received by the lens 306, which collimates the light, and which is received by the beam splitter 305. The beam splitter 305 directs at least a portion of the reflected light to the pupil plate 312 that includes a plurality of pupils 314 arranged to select the desired channels, e.g., multiple angles of incidence. As illustrated in FIG. 7, the optical axis OA of the optical metrology device 300 is normally incident on the sample 101, and thus, optical metrology device 300 is referred to as a normally incident optical metrology device despite the ability to measure multiple angles of incidence using the pupil plate 312. Each pupil 314 in the pupil plate 312 passes a portion of the collimated beam of light 304 to form a beamlet 316. Each beamlet 316 corresponds to a different small cone angle of incident and reflected light. The cone angle that corresponds to each beamlets 316 is illustrated in FIG. 7 with dotted lines between the sample 101 and the pupil plate 114. The beamlets corresponding to different angles of incidence are detected by one or more detectors 320.

Figure 8:
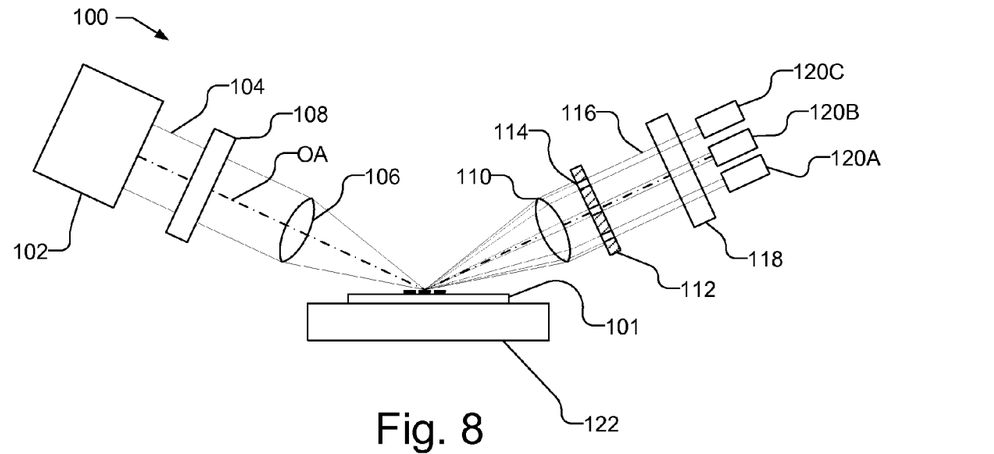
FIG. 8 is a side view of an optical metrology device, similar to that shown in FIG. 1A, and that uses a plurality of separate detectors.

As discussed above in reference to FIG. 1A, the beamlets 116 corresponding to different angles of incidence may be detected by one or more detectors 120. FIG. 8 is a side view of optical metrology device 100, similar to that shown in FIG. 1A, like designated elements being the same, but including a plurality of detectors 120A, 120B, and 120C. As illustrated in FIG. 8, each detector 120A, 120B, and 120C simultaneously detects a different beamlet 116. The plurality of detectors 120A, 120B, and 120C may provide its respective data to computer 130 shown in FIG. 1A.

Figure 9:
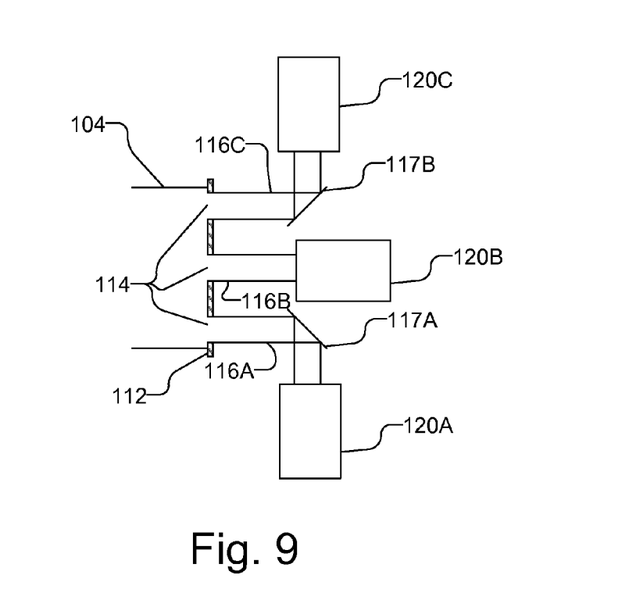
FIG. 9 illustrates a configuration of a plurality of detectors.

FIG. 9 illustrates one configuration for detecting the plurality of beamlets 116 using the plurality of detectors 120A, 120B, and 120C. As illustrated, portions of the beam of light 104 pass through the pupils 114 of the pupil plate 112 to produce beamlets 116A, 116B, and 116C. Beamlet 116B is received by detector 120B, while beamlets 116A and 116C may be incident on folding mirrors 117A and 117B before being received by detectors 120A and 120C, respectively.

Figure 10:
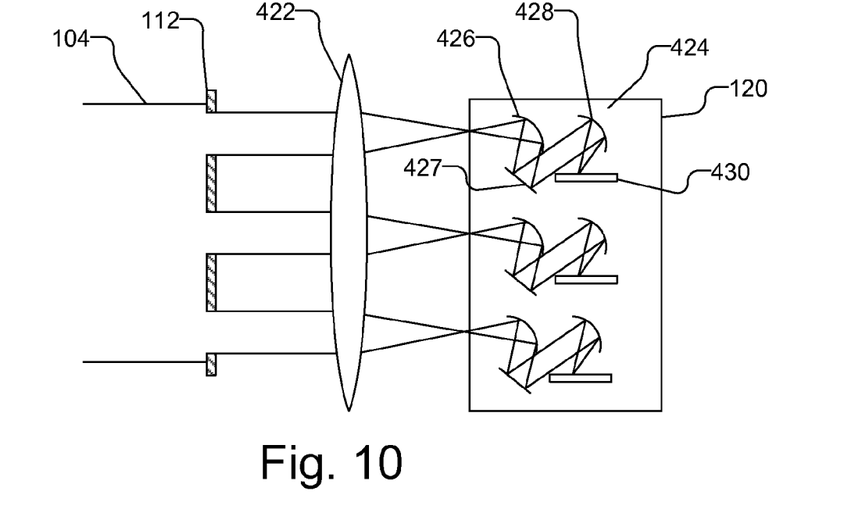
FIG. 10 illustrates a configuration of a single detector with a plurality of spectrophotometers.

FIG. 10 illustrates another configuration for detecting the plurality of beamlets 116. FIG. 10 illustrates a single detector 120 that includes a plurality of spectrophotometer system includes separate CCD arrays. As illustrated, a lens 422 may be used to focus the beamlets 116 on apertures in the detector 120. Each beamlet 116 is received by a separate spectrophotometer system 424 that is illustrated with a number of reflective elements 426 and 427, wavelength scattering element 428, and a CCD array 430. Thus, each CCD array 330 receives the spectra from a different beamlet 116 so that each channel represented by the beamlets 116 may be quickly and efficiently processed with the resulting data provided to the computer 130 (shown in FIG. 1A).

Figure 11:
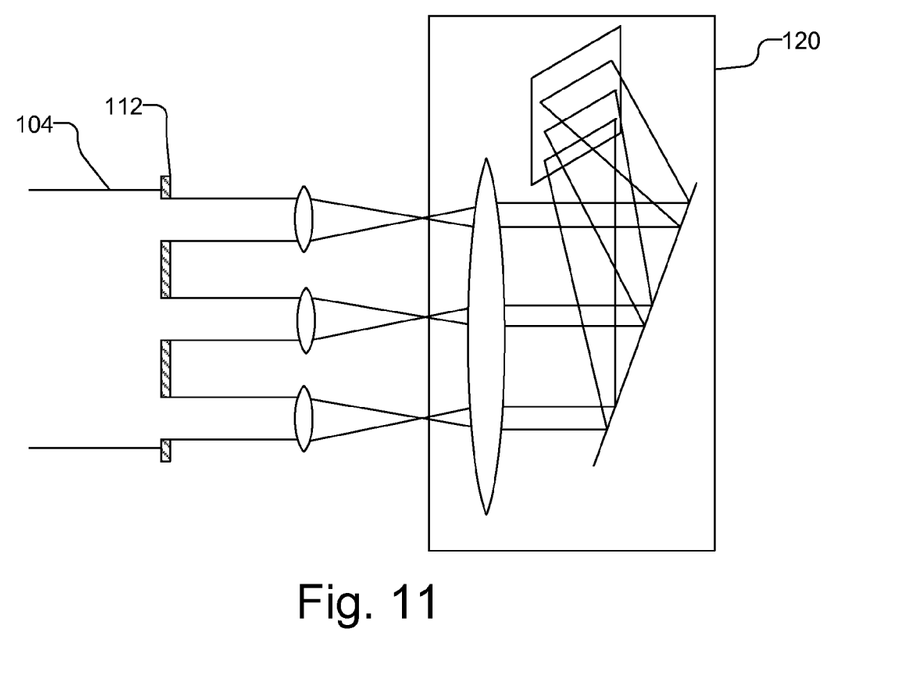
FIG. 11 illustrates a configuration of a single detector with a single spectrophotometer and a two-dimensional CCD array.

FIG. 11 illustrates another configuration for detecting the plurality of beamlets 116. FIG. 11 illustrates a single detector 120 that includes a single spectrophotometer system with a single two-dimensional CCD array. As illustrated, a number of lenses 522 may be used to focus the beamlets 116 on apertures in the detector 120. A spectrophotometer system 524 includes, e.g., a lens 526, a wavelength scattering element 528, and a two dimensional CCD array 530. As illustrated in FIG. 11, each beamlet 116 is simultaneously received by the CCD array 530 and the resulting data provided to the computer 130 (shown in FIG. 1A).

Figure 12:
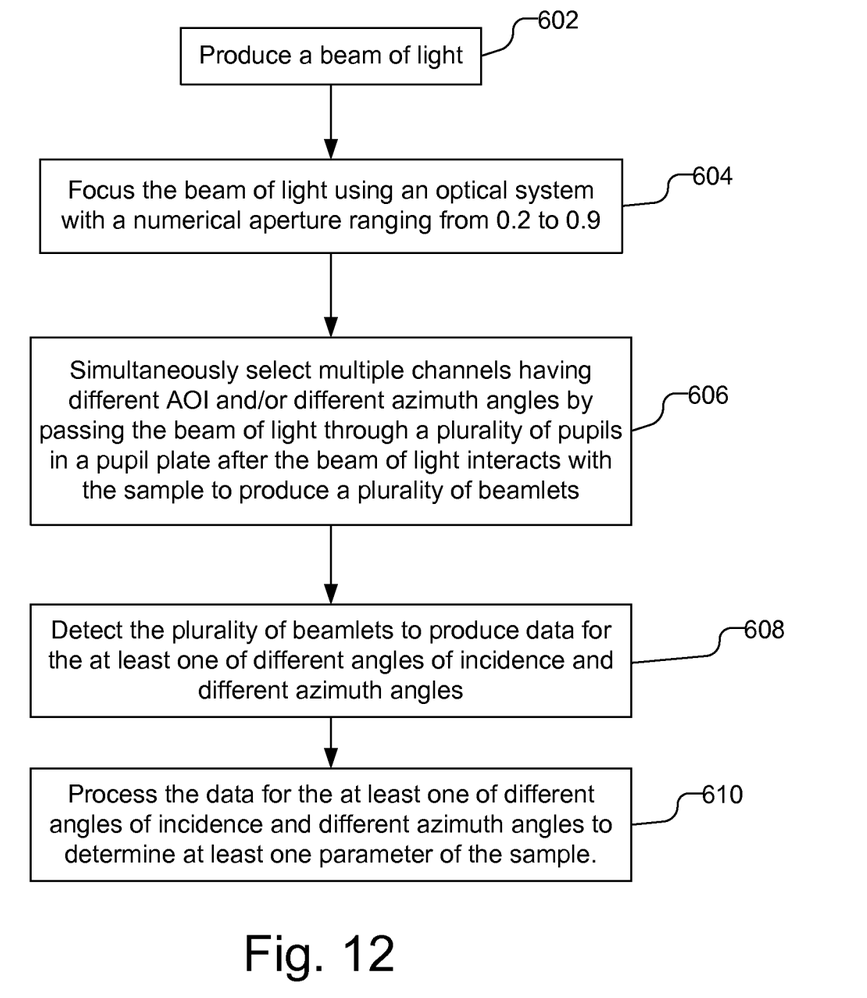
FIG. 12 is a flow chart of a method of using an optical metrology device that is capable of simultaneously selecting multiple channels having different AOI and/or different azimuth angles to determine a characteristic of a sample.

FIG. 12 is a flow chart of a method of using an optical metrology device that is capable of simultaneously selecting multiple channels having different AOI and/or different azimuth angles to determine a characteristic of a sample. As illustrated, the optical metrology device produces a beam of light (602), which may be broad band light or single wavelength. The beam of light is focused to be incident on a spot on a sample using an optical system with a numerical aperture ranging from 0.2 to 0.9. By way of example, the optical system may have a numerical aperture that produces light having a full cone angle that is greater than 23°. Multiple channels are simultaneously selected; the multiple channels have at least one of different angles of incidence and different azimuth angles (606) by passing the beam of light through a plurality of pupils in a pupil plate after the beam of light interacts with the sample. Thus, a plurality of beamlets are produced having the at least one of different angles of incidence and different azimuth angles. If desired, a first plurality of pupils may be used to produce beamlets at a plurality of angles of incidence and a second plurality of pupils may be used to produce beamlets at a plurality of azimuth angles. The plurality of beamlets are detected to produce data for the at least one of different angles of incidence and different azimuth angles (608). For example, the beamlets may be detected using separate detectors or a single detector with separate spectrophotometer systems or a single spectrophotometer system with a two dimensional CCD array. The data for the at least one of different angles of incidence and different azimuth angles may then be processed to determine at least one parameter of the sample, which may then be stored in memory 134 (FIG. 1A) or other storage. For example, the data with the at least one of different angles of incidence and different azimuth angles may be processed to determine at least one of profile parameters and overlay error for the sample. The light may be obliquely incident on the sample and the beam of light collimated after the beam of light interacts with the sample and before simultaneously selecting multiple channels. Alternatively, the optical axis of the light may be normally incident on the sample. The optical metrology device may be an ellipsometer or a reflectometer and may polarize the beam of light before the beam of light is incident on the sample and may analyze the beam of light with a polarizer after the beam of light interacts with the sample.

The process of analyzing the metrology data obtained by the optical metrology device 100 may vary depending, e.g., on the type of parameter or parameters being measured and the configuration of the sample. In one embodiment, for example, the sample may include a diffracting structure, where the optical metrology data is obtained by detecting the zeroth order diffraction from the diffracting structure for each angle of incidence and/or azimuth angle. If desired, however, additional orders of the diffraction, e.g., the ±1st orders, may also be detected. The optical metrology data may be analyzed in the original data format or other converted or transformed formats, for example, linear combination, principal components, etc. The sample structure may include two dimensional lines or three dimensional structures. The profile parameters of the diffracting structure may include, e.g., a shape of lines, holes or islands, linewidth or line length, height, and wall angle of the diffracting structure and overlay shifts. Alternatively, the parameters may be, e.g., at least one of an optical index and film thickness of one or more films on the sample. Alternatively, the metrology data may be analyzed to determine overlay error, e.g., where the sample 101 includes overlying structures.

In one embodiment, the analysis of the optical metrology data may use real time regression, where the measurement data is compared to calculated data by real time calculations and parameters are determined by a nonlinear regression method, an optimization process to minimize the mean square error (MSE) between measurement data and the calculated data. The real time calculation may include Rigorous Couple Wave Analysis (RCWA), finite element, finite difference and machine learning methods. In another embodiment, the analysis of the optical metrology data may be done by a database or library method. The optical metrology data may be compared to a database or library that includes a plurality of functions, where each of the functions corresponds to the one or more parameters of the sample and the optical metrology data, which may be combined or compared to the reference database or library separately.

There may be different ways to determine the parameters in data analysis. In one case, all the parameters are determined in one step analysis, where all the metrology data are analyzed simultaneously. In another case, multiple steps of analysis may be used and for each step, partial parameters may be determined by partial data set. The data analysis may also include using different weights for different metrology data set to enhance the parameter sensitivity or reduce parameter correlation.

Although the present disclosure is illustrated in connection with specific embodiments for instructional purposes, the present invention is not limited thereto. Various adaptations, modifications and combinations of embodiments may be made without departing from the scope of the invention. Therefore, the spirit and scope of the appended claims should not be limited to the foregoing description.

What is claimed is:

1. An optical metrology device comprising:
   a light source that produces a beam of light;
   an optical system that focuses the beam of light into a spot on a sample, the optical system having a numerical aperture ranging from 0.2 to 0.9, an optical axis of the beam of light is obliquely incident on the sample;
   a pupil plate having a plurality of pupils all of which simultaneously receive the beam of light after interacting with the sample, wherein a portion of the beam of light passes through each of the plurality of pupils as a beamlet, the plurality of pupils being arranged to produce beamlets at a plurality of at least one of angles of incidence and azimuth angles;
   at least one detector positioned to receive the beamlets; and
   a processor coupled to receive data from the at least one detector for the plurality of at least one of angles of incidence and azimuth angles, the processor configured to determine at least one parameter of the sample based on the data for the plurality of at least one of angles of incidence and azimuth angles.

2. The optical metrology device of claim 1, wherein the optical system produces light having a full cone angle that is at least 23°.

3. The optical metrology device of claim 1, further comprising a polarizer state controller through which the beam of light passes through before being incident on the sample.

4. The optical metrology device of claim 1, further comprising a polarization state analyzer through which at least a portion of the beam of light passes after before being incident on the sample.

5. The optical metrology device of claim 1, further comprising a second optical system that receives the beam of light after interacting with the sample, the second optical system is positioned between the sample and the pupil plate.

6. The optical metrology device of claim 1, wherein the plurality of pupils comprises a first plurality of pupils to produce beamlets at a plurality of angles of incidence and a second plurality of pupils to produce beamlets at a plurality of azimuth angles.

7. The optical metrology device of claim 1, wherein the at least one detector comprises a plurality of separate detectors receiving the plurality of beamlets.

8. The optical metrology device of claim 1, wherein the at least one detector comprises a single detector having a plurality of spectrophotometer systems receiving the plurality of beamlets.

9. The optical metrology device of claim 1, wherein the at least one detector comprises a single detector having a spectrophotometer system with a two dimensional CCD array that simultaneously receives the plurality of beamlets.

10. The optical metrology device of claim 1, wherein the at least one parameter of the sample comprises at least one of profile parameters and overlay error.

11. A method comprising:
    producing a beam of light;
    focusing the beam of light to be incident on a spot on a sample using an optical system with a numerical aperture ranging from 0.2 to 0.9, an optical axis of the beam of light is obliquely incident on the sample;
    simultaneously selecting multiple channels having at least one of different angles of incidence and different azimuth angles by passing the beam of light through a plurality of pupils in a pupil plate after the beam of light interacts with the sample to produce a plurality of beamlets having the at least one of different angles of incidence and different azimuth angles;
    detecting the plurality of beamlets to produce data for the at least one of different angles of incidence and different azimuth angles; and
    processing the data for the at least one of different angles of incidence and different azimuth angles to determine at least one parameter of the sample.

12. The method of claim 11, wherein the optical system produces light having a full cone angle that is at least 23°.

13. The method of claim 11, further comprising polarizing the beam of light before the beam of light is incident on the sample.

14. The method of claim 11, further comprising analyzing the beam of light after interacting with the sample using a polarizer.

15. The method of claim 11, further comprising collimating the beam of light after the beam of light interacts with the sample and before simultaneously selecting multiple channels.

16. The method of claim 11, wherein the plurality of pupils comprises a first plurality of pupils to produce beamlets at a plurality of angles of incidence and a second plurality of pupils to produce beamlets at a plurality of azimuth angles.

17. The method of claim 11, wherein detecting the plurality of beamlets to produce data comprises detecting each beamlet with a separate detector.

18. The method of claim 11, wherein detecting the plurality of beamlets to produce data comprises detecting each beamlet with a separate spectrophotometer system in a single detector.

19. The method of claim 11, wherein detecting the plurality of beamlets to produce data comprises simultaneously detecting each beamlet with a single spectrophotometer system having a two dimensional CCD array in a single detector.

20. The method of claim 11, wherein the at least one parameter of the sample comprises at least one of profile parameters and overlay error.

21. An optical metrology device comprising:
a light source that produces a beam of light;
an optical system that focuses the beam of light into a spot on a sample, the optical system having a numerical aperture ranging from 0.2 to 0.9, an optical axis of the beam of light is obliquely incident on the sample;
a channel selector configured to receive the beam of light after interacting with the sample and simultaneously selecting multiple channels having at least one of different angles of incidence and different azimuth angles;
at least one detector positioned to detect the multiple channels to produce data for the at least one of different angles of incidence and different azimuth angles; and
a processor coupled to receive the data from the at least one detector, the processor configured to determine at least one parameter of the sample based on the data for the at least one of different angles of incidence and different azimuth angles.

22. The optical metrology device of claim 21, wherein the optical system produces light having a full cone angle that is at least 23°.

23. The optical metrology device of claim 21, wherein the optical metrology device is an ellipsometer.

24. The optical metrology device of claim 21, wherein the channel selector comprises a first plurality of pupils arranged to transmit light having a plurality of angles of incidence and a second plurality of pupils arranged to transmit light having a plurality of azimuth angles.

25. The optical metrology device of claim 21, wherein the at least one parameter of the sample comprises at least one of profile parameters and overlay error.

* * * * *